(12) United States Patent
Summer et al.

(10) Patent No.: US 9,453,247 B2
(45) Date of Patent: *Sep. 27, 2016

(54) APPLICATION OF BACTERIOPHAGES FOR THE CONTROL OF UNWANTED BACTERIA IN BIOFUEL PRODUCTION MEDIATED BY NON-BACTERIAL REACTIVE AGENTS

(75) Inventors: Elizabeth J. Summer, College Station, TX (US); Mei Liu, College Station, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/465,700

(22) Filed: May 7, 2012

(65) Prior Publication Data

US 2013/0149753 A1    Jun. 13, 2013

Related U.S. Application Data

(60) Provisional application No. 61/489,764, filed on May 25, 2011.

(51) Int. Cl.
| | | |
|---|---|---|
| C12P 7/64 | (2006.01) | |
| C12P 7/06 | (2006.01) | |
| C12N 7/02 | (2006.01) | |
| C12P 7/10 | (2006.01) | |

(52) U.S. Cl.
CPC . *C12P 7/64* (2013.01); *C12N 7/02* (2013.01); *C12P 7/06* (2013.01); *C12P 7/10* (2013.01); *C12N 2795/00031* (2013.01); *Y02E 50/13* (2013.01); *Y02E 50/16* (2013.01); *Y02E 50/17* (2013.01); *Y02E 50/343* (2013.01)

(58) Field of Classification Search
CPC ............. C12P 7/16; C12P 19/14; C12P 7/10; C12P 19/02; C12P 5/007; C12P 7/06; C12P 7/40; C12P 7/42; C12P 2201/00; C12P 5/026; C12P 7/065; C12P 7/14; C12P 7/18; C12P 13/02; C12P 2203/00; C12P 5/02; C12P 7/04; C12P 7/46; C12P 7/58
USPC ...................................... 435/161, 134, 235.1
See application file for complete search history.

(56) References Cited

U.S. PATENT DOCUMENTS

| | | | |
|---|---|---|---|
| 3,105,014 A | 9/1963 | Harrison | |
| 4,442,895 A | 4/1984 | Lagus et al. | |
| 4,778,653 A | 10/1988 | Kamimura et al. | |
| 5,160,433 A | 11/1992 | Nielson et al. | |
| 5,441,873 A | 8/1995 | Knight et al. | |
| 6,926,833 B2 | 8/2005 | Van Reis | |
| 7,256,160 B2 | 8/2007 | Crews et al. | |
| 7,674,467 B2 | 3/2010 | Sulakvelidze | |
| 7,882,895 B2 | 2/2011 | Kabishcher et al. | |
| 8,168,419 B2 | 5/2012 | Baldwin et al. | |
| 8,241,498 B2 * | 8/2012 | Summer .................. | C02F 3/348 210/606 |
| 8,241,499 B2 | 8/2012 | Liu et al. | |
| 8,252,519 B2 | 8/2012 | Baldwin et al. | |
| 8,252,576 B2 | 8/2012 | Campbell et al. | |
| 8,585,899 B2 | 11/2013 | Baldwin et al. | |
| 2006/0094076 A1 * | 5/2006 | Stave ........................ | C12N 7/00 435/34 |
| 2008/0213752 A1 | 9/2008 | Stave et al. | |
| 2009/0104157 A1 * | 4/2009 | Solomon et al. ............ | 424/93.6 |
| 2009/0180992 A1 | 7/2009 | Summer et al. | |
| 2009/0246336 A1 | 10/2009 | Burnett et al. | |
| 2011/0053144 A1 * | 3/2011 | Garcia Aljaro et al. .......... | 435/5 |
| 2011/0281329 A1 | 11/2011 | Lenherr et al. | |
| 2013/0149759 A1 | 6/2013 | Summer et al. | |
| 2014/0061123 A1 | 3/2014 | Summer et al. | |
| 2014/0102975 A1 * | 4/2014 | Summer .................. | C02F 3/348 210/601 |
| 2014/0273159 A1 | 9/2014 | Summer et al. | |

FOREIGN PATENT DOCUMENTS

| | | |
|---|---|---|
| JP | 02099196 | 4/1990 |
| WO | WO-02/40642 | 5/2002 |
| WO | WO 2006/050193 | 11/2006 |
| WO | WO-2008/078978 | 7/2008 |

OTHER PUBLICATIONS http://en.wikipedia.org/wiki/Biofilm (last visited on Jun. 10, 2013).*
Abedon, S. et al. Experimental Examination of Bacteriophage Latent-Period Evolution as a Response to Bacterial Availability, Applied and Environmental Microbiology, Dec. 2003, 69 (12): 7499-7506.
Lu, T.K. et al., Dispersing biofilms with engineered enzymatic bacteriophage, PNAS, Jul. 2007, 104 (27): 11197-11202.
Zacheous, O.M. et al., Soft deposits, the key site for microbial growth in drinking water distribution networks, Water Research, May 2001, 35 (7): 1757-1765.
Scholtens, et al., ("Phage Typing of Salmonella Typhi in the Netherlands", from the Rijks Instituut voor de Volksgezondheid, Utrecht; Jun. 6, 1950).
Greenberg, et al., ("Tracing Typhoid Carriers by Means of Sewage", presented at the 1957 annual meeting, California Sewage and Industrial Wastes Assn.; San Diego, CA.; May 1-4, 1957).
Derwent Translation of Araki et al. (JP 02099196) of Apr. 1990.
Sakaguchi, et al., (Control of Microbiofouling Using Bacteriophage 2. Detection of Phages and Fundamental Study of their Lytic Effect on Fouling Bacteria (Abstract Only), DE.
Lee, et al., (Molecular analysis of a mixed-species biofilm on carbon steel. Abstracts of the General Meeting of the American Society for Microbiology. 2003; vol. 103:Q-156.
Jiang, S.C. et al., Significance of lysogeny in the marine environment: studies with isolates and a model of lysogenic phage production, Microbial Ecology, May 1998, 35 (3): 235-243.

(Continued)

Primary Examiner — Kagnew H Gebreyesus
Assistant Examiner — Nghi Nguyen
(74) Attorney, Agent, or Firm — Tifani M. Edwards

(57) ABSTRACT

A method of reducing process interruptions in biofuel production systems by reducing the amount of unwanted bacteria in the biofuel production system in which the reduction is effected by the use of an effective amount of one or more types of bacteriophages virulent for at least some strains of the unwanted bacteria.

11 Claims, 2 Drawing Sheets

(56) References Cited

OTHER PUBLICATIONS

McNair, et al., (Predicting Phage Preferences: Lytic vs. Lysogenic Lifestyle from Genomes. 2013 from the San Diego State University).

Fortier, L.C. et al., Importance of Prophages to Evolution and Virulence of Bacterial Pathogens, Virulence, Jul. 2013, 4(5): 354-365.

Office Action dated Mar. 17, 2016 in related U.S. Appl. No. 14/060,297, filed Oct. 22, 2013.

Office Action dated May 19, 2015 in related U.S. Appl. No. 14/060,297, filed Oct. 22, 2013.

Applicant's Response dated Oct. 19, 2015 to the Office Action in related U.S. Appl. No. 14/060,297, filed Oct. 22, 2013.

Office Action dated Mar. 20, 2015 in related U.S. Appl. No. 14/056,808, filed Oct. 17, 2013.

Applicant's Response dated Apr. 3, 2015 to the Office Action in related U.S. Appl. No. 14/056,808, filed Oct. 17, 2013.

Office Action dated Apr. 23, 2015 in related U.S. Appl. No. 14/056,808, filed Oct. 17, 2013.

Applicant's Response dated Oct. 23, 2015 to the Office Action in related U.S. Appl. No. 14/056,808, filed Oct. 17, 2013.

Applicant's Response dated Apr. 29, 2016 to the Office Action in related U.S. Appl. No. 14/056,808, filed Oct. 17, 2013.

Office Action dated May 19, 2015 in related U.S. Appl. No. 14/133,115, filed Dec. 18, 2013.

Applicant's Response dated Oct. 19, 2015 in related U.S. Appl. No. 14/133,115, filed Dec. 18, 2013.

Office Action dated Jan. 29, 2016 in related U.S. Appl. No. 14/133,115, filed Dec. 18, 2013.

\* cited by examiner

APPLICATION OF BACTERIOPHAGES FOR THE CONTROL OF UNWANTED BACTERIA IN BIOFUEL PRODUCTION MEDIATED BY NON-BACTERIAL REACTIVE AGENTS

RELATIONSHIP TO OTHER APPLICATIONS

This application claims benefit of and priority from application 61/489,764 filed May 25, 2011.

FIELD OF THE INVENTION

This invention relates to a method of reducing process interruptions in biofuel production systems by reducing the amount of unwanted bacteria in the biofuel production system. More specifically, the reduction is effected by the use of an effective amount of one or more types of bacteriophages virulent for at least some strains of the unwanted bacteria.

BACKGROUND

Biofuels including alcohol or lipid and oil based products that are derived from biological sources are gaining wide consumer and regulatory acceptance as renewable fuels. Widespread commercialization of oils extracted from plant and animal materials (primarily, but not limited to seed oils) as well as alcohols (including but not limited to ethanol, methanol and butanol) produced by the microbial fermentation of simple sugars and starches has already occurred. The fermentable substrate material is commonly referred to as "feedstock". Commercial biofuel grade alcohol production can utilize feedstocks of simple sugars and starch sources including seeds (including but not limited to corn seed, wheat seed) as well as high sugar or simple starch content plant materials such as sugar beets, molasses, and sugar cane extracts. Feedstocks under evaluation for alcohol fermentation substrate also include the remaining parts of the plant and waste plant materials such as woody portions, husks, seed coatings, leafy materials, roots, fibrous material. These substrates are sometimes referred to as lignocellulosic, biomass, or cellulosic feedstocks. Still other fuel types include flammable gasses such as biogas, biohydrogen, etc.

There has been an increasing trend to rely on microbial fermentation activities in converting biomass into burnable fuels. The general process involves hydrolysis of the biomass (physical, chemical, and/or enzymatic) into fermentable substrates, and then microbes (including microalgae, fungi, and bacteria) ferment the substrates into biofuels. Another microbial source of biofuels is the production of lipids, especially triacyglycerides (TAG) by oleaginous microorganisms, including algae and fungi. Oil producing microorganisms are those that produce lipids and oils that can be converted into fuel quality lipids and oils. Of particular note is the production of biodiesels by algae.

Any biofuel generating process that utilizes microbial activity is subject to production slowdowns, failures, or reduction in production efficiencies through the activity of undesirable or contaminating microorganisms. The desired, biofuel producing organisms may be fungal, algal, including all clades of algae regardless of taxonomic position, or protozoan and the biofuel product may be alcohols, lipids and oils, or gas.

As a common form of biofuel, bioethanol is being widely used in many countries as motor fuels. In the U.S., fuel ethanol production has increased from 1.7 billion gallons in 2000 to almost 12.5 billion gallons in 2009 (www.ethanol-rfa.org/pages/statistics). The number of ethanol fermentation facilities is also rapidly increasing, from 110 U.S. plants operating in 2007 to 187 in 2010. Bioethanal fermentation facilities utilize microbial activities to convert agricultural feedstocks into ethanol. The majority of commercial bioethanol fermentation plants in the U.S. are designed to utilize a grain feedstock, primarily corn, which is fermented by microorganisms, especially yeast, into ethanol. In standard operation, the complex carbohydrate chemistry of the feedstock is converted into simpler sugars by a combination of enzymatic (e.g. amylase or other starch-hydrolyzing enzyme) and/or physical (e.g. temperature and shearing) and/or chemical (e.g. by treatment with dilute sulfuric acid or other chemicals) treatment, forming a liquefied mash. Simple sugars in the liquefied mash are then used as substrates for ethanol fermentation by yeast. Cellulosic and lignocellulosic feedstocks are an attractive alternative to grain feedstocks, although they present additional challenges in terms of preparing the fermentable substrate. Because grain feedstock fermentation facilities utilizing yeast for ethanol production almost exclusively comprise current commercial operations, bacterial problems at these facilities are used in this application as illustrative examples of the method herein disclosed, and comprise a preferred aspect of this invention.

Example of the Target: Unwanted Bacteria in Ethanol Production

Chronic and acute bacterial contamination of the fuel ethanol fermentation process is common. Bacteria may initially enter the process with the feedstock or be present at the facility, for example on equipment, in liquids or in biofilms that serve as reservoirs for the bacteria. Bacteria may persist in the fermenters, along piping turns, and in heat exchangers and valves. While bacterial levels vary during the different steps for preparing the grain substrate for fermentation, by the time the processed mash is ready for yeast inoculation, the total bacterial levels in a normal, "healthy" fermentation facility are around $10^6$ colony forming units (CFU) per ml in a wet mill and as high as $10^8$ CFU/ml in a dry-grind facility (Skinner and Leathers 2004). However, bacterial levels higher than this frequently develop, negatively impacting ethanol yields. The most widely cited agents responsible for fuel ethanol fermentation slowdown are lactic acid bacteria (LAB), primarily members of the Gram-positive genera *Lactobacillus, Pediococcus, Leuconostoc* and *Weissella* (Bischoff, Liu et al. 2009). Bacteria inhibit the yeast fermentation process through the competitive consumption of sugars, which bacteria convert into organic acids instead of ethanol. These organic acids, primarily lactic and acetic, are inhibitory to the vitality of the yeast. Infections may be chronic, resulting in an overall constant loss of production efficiency, or acute, resulting in stagnated—or "stuck"—fermentation that requires the system be shut down for decontamination. Depending on the feedstock, fermentation system employed, and the nature of the contaminant, estimates on ethanol losses range from 1% for chronic infections to over 20% for extreme stuck fermentations (Bischoff, Liu et al. 2009, Makanjuola, Tymon et al. 1992, Narendranath, Hynes et al. 1997). Even a 1% decrease in ethanol yield is significant to ethanol producers (Narendranath 2003). At an average 50 million gallons per year (mgy) plant, a 1% loss equates to a decrease of 500,000 gallons of ethanol per year. Based on an average spot price of $1.84 per gallon (average for 2010, data available at www.neo.ne.gov/statshtml/66.html), this represents a loss of $920,000 in annual revenue.

While more data is available on the impact of bacteria on grain feedstock utilizing facilities, pilot plants utilizing lignocellulosic or biomass feedstock are also subject to contamination by undesirable bacteria (Schell, Dowe et al. 2007). It is anticipated that as more biomass and lignocellulosic alcohol fermentation facilities become operational, issues with bacterial contamination will also manifest. Additionally, biodiesel production using oleaginous algal or fungal or protozoan cultures are already known to be subject to production slowdowns due to invasive bacteria.

Regardless of the biofuel being generated, biofuel production can be negatively impacted by the activity of unwanted, invasive or contaminating bacteria. The scope of this invention covers all forms of biofuel production regardless of chemistry of the biofuel product or identity of the biofuel-producing organisms. Any biofuel production process that is negatively impacted by contaminating bacteria is covered by the scope of the invention. However, due to the abundance of information on ethanol production in corn fermentation facilities, this will be the example used to illustrate the method.

Control of Unwanted Bacteria: The LAB in Corn Ethanol Fermentation
Current Control Methods Bacterial control methods have an immediate positive impact and even a simple one-log reduction in the amount of LAB can increase ethanol yield by approximately 3.7% (Bischoff, Liu et al. 2009). Bacterial contamination in fuel ethanol plants is typically controlled by a combination of plant management approach and through the addition of chemical antimicrobials and antibiotics. The types and amounts of chemicals that can be used to control LAB are limited because the compounds must reduce bacteria without affecting the yeast culture and must also not carry over as harmful residue in the solid co-products of fuel ethanol fermentation, which is frequently sold as distillers dried grains with solubles (DDGS) for animal feeds. The plant management approach involves the routine cleaning of equipment and reactors, as well as controlling physical and chemical parameters such as temperature, pH, and acid levels to favor yeast over bacterial growth. Chemical antimicrobials that can be added to reduce bacterial levels include typical quaternary compounds and gluteraldehyde, as well as more specialized formulations such as a stabilized $ClO_2$ product sold by DuPont under the trade name FermaSure™.

Challenges Associated with Antibiotic Use

Not surprisingly, antibiotics, in particular virginiamycin and penicillin, have been found particularly effective in curbing bacterial populations without disturbing the yeast. This has led to the widespread use of antibiotics in the fuel ethanol fermentation industry. However, antibiotic residue has been detected in the solid distillers grain residue (DG) that is sold as livestock feed (De Alwis and Heller). Additionally, there is evidence that antibiotic use leads to selection for antibiotic resistance (Bischoff, Skinner-Nemec et al. 2007). Even though effective, it is generally agreed that there needs to be an end to indiscriminate, non-therapeutic use of antibiotics. Thus, the ethanol industry in particular, and the biofuel industry in general, needs to move quickly to replace antibiotics.

Bacteriophage Control of Unwanted Bacteria

Bacteriophage, or phage, are the viral predators and parasites of bacteria. Included in this definition are the dsDNA (double stranded DNA genome) tailed phages, referred to as the Caudovirales, or sometimes the caudoviruses, caudophage or tailed phage. Among the tailed phages included here are members of the three morphotypes, including the contractile tailed Myoviridae, the long non-contractile tailed Siphoviridae, and the short tailed Podoviridae. It should be noted that these morphological distinctions do not reflect phylogenetic relationships based on genetic analysis and so no implication of relatedness in inferred by this classification system. Also included in the definition of phage are the phages classified based on genome composition, morphology, and presence or absence of a lipid envelope, including the Tectiviridae, Corticoviridae, Lipothrixviridae, Plasmaviridae, Rudiviridae, Fuselloviridae, Inoviridae, Microviridae, Leviviridae, and Cystoviridae. As taxonomic classifications are frequently updated based on new techniques, such as molecular data, these definitions of phages includes any new phage families that might be created. It should also be noted that these phage families includes members often referred to as viruses of Archaea.

Historical and Current Commercial Phage Use

The bacteriolytic nature of phages leads to interest in their use as antimicrobials. Phage themselves are not new, having been discovered during the First World War. The most obvious use of phages is for medical applications. While early interest in phage therapy was suppressed by the introduction of antibiotics, the recent rise in antibiotic resistance and costly food contamination events has led to a resurgence of interest in phages (Kropinski 2006; Mattey and Spencer 2008; Housby and Mann 2009). In the United States, phages have been applied on human patients as part of a more comprehensive approach to controlling and curing chronic wounds associated with diabetic ulcers and pressure wounds. The commercial development of phages to treat infections in humans is crippled by the expensive regulatory requirements for new drug approval. This problem is exacerbated by the ambiguous classification of phages within the context of drug testing protocols. In contrast, the application of phages in food and agriculture faces fewer challenges and many applications are under investigation (Sabour and Griffiths 2010). In 2007, phages were approved by the FDA as a food additive, specifically for the control of the food-borne pathogen *Listeria* on commercial luncheon meats (Bren 2007). Commercial phage products sold in the U.S. include AgriPhage, sold by Omnilytics and designed to control *Xanthomonas* infestations in peppers and tomatoes and Finalyse, sold by Elanco Foods and designed to control *E. coli* 0157:H7 levels on slaughterhouse cattle.

Advantages of Phages for Use in Biofuel Production

Phages are natural, ubiquitous bacteriolytic agents with extremely high host specificity. Phage formulations and antibiotics both have advantages over chemical biocides in that they specifically kill target unwanted host bacteria without interacting with non-bacterial microorganisms (such as yeast or algae) responsible for alcohol or oil production. In contrast, chemical biocides are much less selective and doses effective against bacteria may adversely modulate growth of the biofuel producing organisms. Thus, the present innovative application of phages to control unwanted bacteria in the biofuel production process will lead to both immediate economic and long-term socioeconomic impacts.

SUMMARY OF THE INVENTION

The invention described herein is a method of reducing the concentration of unwanted bacteria in biofuel production processes, which utilize eukaryotic organisms to produce or metabolize the biofuel or biofuel. Any eukaryotic organism includes fungi, yeasts, eukaryotic algae from any of the algal clades, protozoan or even animals and plants. This is in contrast to biofuel production systems that utilize prokaryotic, including bacterial and archaeal, One or more bacteriophage panels, which are comprised of one or more bacteriophages virulent for one or more strains of the unwanted bacteria, are applied to some aspect of the biofuel production process to reduce the concentration of unwanted bacteria in said process.

When used in alcohol fermentation systems, using yeast or any other alcohol fermentative organism, the invention will result in improved fermentation efficiencies, reduced wastes, and reduced antibiotic residue in solid byproducts. When used to control contaminating bacteria during the culturing of a lipid producing eukaryotic organism, such as an algae, oil production levels are expected to increase due to increased densities of the oleaginous organism.

In a preferred embodiment, the biofuel production process is an ethanol formation process comprised of fermentation of suitable feedstocks, wherein the control of unwanted bacteria is effected by bacteriophages assembled into one or more bacteriophage panels such that one or more bacteriophage strains in each panel is virulent for one or more of the unwanted bacteria. In another more preferred embodiment, the biofuel production process is an oil or lipid producing system that utilizes culturing of oleaginous eukaryotes, for example an algae or fungus, wherein the control of unwanted bacteria is effected by bacteriophages assembled into one or more bacteriophage panels such that one or more bacteriophage strains in each panel is virulent for one or more of the unwanted bacteria. The bacteriophage may originate from exogenous sources or may be concentrated from the sample itself. Bacteriophage may be prepared by matching the contaminant with phages previously collected and maintained in libraries of phages.

In another embodiment, the invention is a dynamic phage multi-panel produced de novo by repetitive or continuous proliferation, concentration, or both proliferation and concentration of bacteriophages resident in the biofuel producing systems, which may be conducted onsite or at a central location.

In another embodiment, treatment to control unwanted bacteria in the biofuel production process may be conducted by bacteriophages in various ways, before operation, during operation or as a prophylactic for cleaning process vessels and equipment.

The invention is also a composition comprising an assembly of one or more bacteriophages virulent for unwanted bacteria in a biofuel production process.

The invention is also a process for control of unwanted bacteria in a biofuel production process which utilizes eukaryotic, or non-bacterial, system organisms, comprising concentrating one or more strains of bacteriophages resident in the biomass to an effective concentration for control of one or more strains of unwanted bacteria.

DETAILED DESCRIPTION

Figure 1:
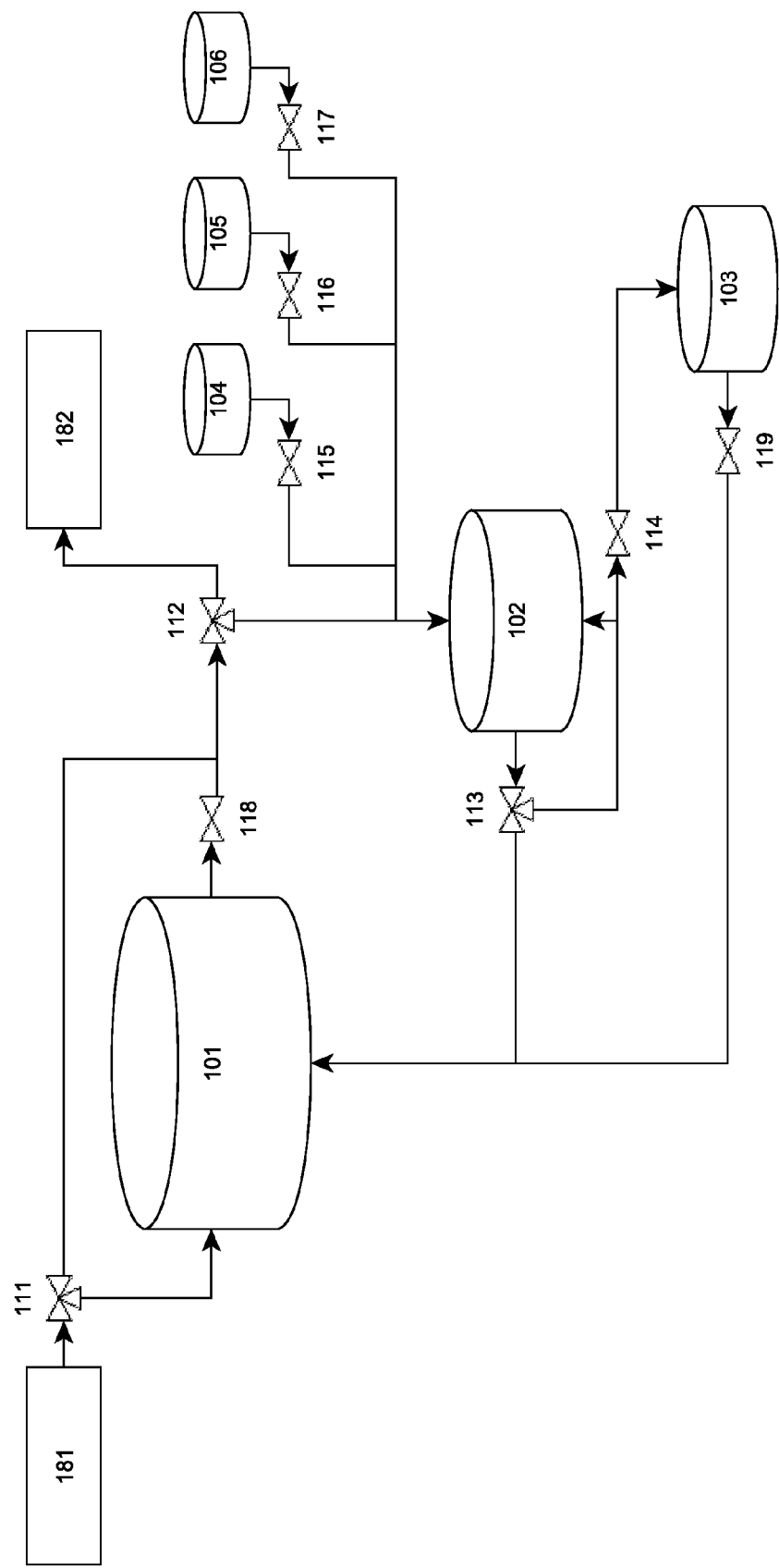
FIG. 1 is a diagrammatic representation of an embodiment of the method of the invention.

The present invention is a method of utilizing bacteriophages to control unwanted bacteria in non-bacterial, or eukaryotic metabolic reaction processes involved in biofuel production. In a preferred aspect, the method is applied to control unwanted lactic acid bacteria (LAB) in the yeast-based fermentation stage of ethanol production. In another preferred aspect, the method is applied to control any unwanted bacteria from the yeast-based fermentation stage of alcohol production. In another preferred aspect, the method is applied to control invasive or contaminating bacteria during the culturing of oleaginous eukaryotes such as algae or fungi for oil extraction to be processed into biodiesel or biogasoline. Application of the invention for yeast-based ethanol fermentation facility is described. As illustrated in FIG. 1, the basic ethanol plant process is depicted as a biomass stream from a previous production step 181 (e.g. hydrolysis) flowing into reactor 101 (e.g. a fermentation tank) and out again to the next production step 182. The invention is comprised of various process embodiments and systems for producing and applying phages to the production process units, particularly fermentation.

Preferred Aspect of Fuel Ethanol Fermentation

Contamination of the fuel ethanol fermentation process by LAB results in significant reduction in ethanol yields. Reducing bacterial contamination by even one or two colony forming unit (CFU) log orders has been found to increase ethanol product (Bischoff et al 2009 In a preferred embodiment of this invention, phages are used to control unwanted bacterial species in sugar/starch and/or lignocellusosic feedstock ethanol plants utilizing a eukaryotic (non-bacterial) fermentative organism such as yeast. In a more preferred embodiment, the unwanted bacterial species targeted are from acetic and lactic acid producing genera, especially those referred to as lactic acid bacteria. In an especially preferred embodiment, the feedstock is grain, with corn most preferred.

Although the present invention is focused on treating LAB in grain feedstock fermentation in particular, and non-bacterially-driven fermentation processes in general, it will be clear to those skilled in the arts of microbiology, biofuel production, and related fields, that the invention may be applied to any similar biofuel production process, so long as: 1) the process is driven by one or more non-bacterial (eukaryotic) or biofuel generative reactive agents, and 2) it is desirable to control one or more unwanted bacterial strains. Examples of alternative embodiments include, but are not limited to, controlling unwanted bacteria in: fermentation of feedstock by fungi; biofuel lipid and oil production using algae (eukaryotic algae), such as is used in the production of some biodiesels; and production of enzymes from fungus (e.g. *Trichoderma reesei*) for immediate or later use in biofuel production.

Definitions

As used herein, it is understood that the terms "phage(s)" and "bacteriophage(s)" are synonymous and includes all of the viral predators and parasites of bacteria. Other terms used herein have the meaning stated below.

The term "biomass," as used herein, refers to "biological material derived from living or recently living organisms. In the context of biomass for energy this is often used to mean plant based material, but biomass can equally apply to both animal and vegetable derived material." Biomass may include, but is not limited to, grain feedstocks (e.g. corn), high-energy feedstocks (e.g. sugar cane), cellulosic and lignocellulosic feedstocks, and plant or animal waste feedstock (including bagasse and other wastes from cellulosic, sugar, and starch biomass used for fuel production or some other process). In the context of this application, the term "biomass" is also understood to refer to any mass, resulting from the original biomass, downstream of the original process. One non-exclusive example would be a lignocellulosic feedstock being referred to as "biomass," while the term "biomass" is also used to refer to the mixture during and after hydrolysis, fermentation, etc.

The term "biomass stream," as used herein, refers to biomass as it moves through a biofuel production system, from the origination of a particular system, through and between each process, and concluding with the final product and waste products.

The term "bioreaction," as used herein, refers to the use of one or more living organisms or enzymes ("system reactive agent(s)"), to convert one or more substrates into one or more products. Examples include, but are not limited to: yeast, algae or fungi ("system reactive agent") metabolizing sugars or other feedstock (substrates) and producing alcohols or lipids and oils (product), bacteria ("system reactive agent") metabolizing a feedstock (substrate) and producing enzymes (product) used in some aspect of biofuel production, or an enzyme (system reactive agent) used to convert carbohydrates (substrate) into sugars (product).

As used herein, the term "reaction" is understood to include, but is not limited to, both chemical reactions and bioreactions.

The term "bioreactor," as used herein, refers to a tank, vat, or other container in which one or more bioreactions and/or culturing of the biofuel producing organism are performed. As used herein, the term "reactor" is understood to include, but is not limited to, tanks, vats, vessels or containers used for performing both chemical reactions and bioreactions.

The term "biofuel," as used herein, refers to any fuel produced from biomass feedstocks. Examples include, but are not limited to: bioethanol; biobutanol; hydrocarbon bio-gasoline, -diesel, or jet fuel (drop-in fuels); biodiesel; chars and tars; biomethanol, and biohydrogen. The term is used regardless of production process or organisms involved.

The phrase "biofuel production system," as used herein, refers to a system, or any part thereof, directly or indirectly involved in the production of biofuel. Examples include, but are not limited to, an ethanol production plant, an algae-based biodiesel plant, and an enzyme production process where at least one use of the enzymes produced is utilized in some aspect of biofuel production. Accordingly, it is understood herein that the term "biofuel production process" is used to refer to any process or processes used by a biofuel production system.

The terms: "reactive agent," "system reactive agent," "system organism," "system microbe," "system microorganism," or "system bacteria," as used herein, refer to the agent(s) responsible for the bioreaction in the particular biofuel production system or process. The system reactive agent(s) need not necessarily be known, isolated, or identified; the sole defining characteristic is that it is the reactive agent(s) desired, ideal, and/or necessary for the desired bioreaction(s) to proceed. System reactive agents may include, but are not limited to: yeast, fungi, algae, protozoans and enzymes.

The term "unwanted bacteria," as used herein, refers to the strain(s) of bacteria specifically targeted for control by the invention described herein. Typically, but not necessarily, the unwanted bacteria is targeted for control because of interference with the reaction(s), such as in the case of unwanted LAB in yeast-based ethanol fermentation. The unwanted bacteria need not necessarily be known, isolated, or identified; the sole defining characteristic is that it is the organism(s) desired to be controlled. This invention provides for reduction of invasive bacteria and other unwanted and problematic bacteria.

The term "phage cocktail," as used herein, includes multiple, preferably receptor independent phages for a single targeted strain of unwanted bacteria. This is different from a "phage panel," which is a collection of phages chosen to target a particular range of host strains. For the purposes of this invention, the phage treatment will be comprised of one or more "phage panels," each comprised of one or more "phage cocktails," that is, there will be one or more virulent phage strains targeting each unwanted bacterial strain and one or more phage cocktails targeting one or more unwanted bacterial strains. Since some phages are known to be polyvalent—effective against more than one strain of bacteria—there may not always need to be a separate cocktail for every strain of unwanted bacteria.

Therefore, as used herein, it is understood that "phage panel(s)" refers in the broadest sense to a combination of one or more phage(s) intended for control of one or more bacterial strains. It encompasses everything from one phage cocktail comprised of one phage strain, to many phage cocktails, each comprised of many phage strains. A "phage multi-panel" refers to one or more phage panels, or the total suite of phage strains used in a particular application.

The terms "assemble", "assembly," "assembled," and their related forms, as used herein in connection to phage cocktail(s), panel(s) and multi-panel(s), refer to choosing and compiling the strain(s) of phages making up the panel(s). This need not include actual identification or isolation of the phages, however, such as in the case of dynamic phage multi-panels discussed hereafter. Assembly of a phage panel does not refer to production or proliferation of the panel.

The terms "proliferate," "proliferating," "proliferation," and their related forms, as used herein in connection to phages and phage cocktail(s), panel(s), and multi-panel(s), refer to the reproduction (growth or increase in quantity) of the phage(s) being referenced. As used herein, the terms are not meant to describe speed of growth or reproduction.

General Description of Method

The fundamental innovation outlined in this invention is use of bacteriophage based formulations for the control of bacteria in the biofuel industry, particularly drawn to LAB in the fuel ethanol fermentation industry. Tailed phages utilize an infection cycle that initiates when the phage tail proteins recognize and adsorb to specific cell surface features of the target bacterial host, followed by injection of the phage DNA into the bacterial cytoplasm. The phage double stranded DNA genome is replicated along with the transcription and translation of virion proteins. New phage particles are assembled, usually, but not always, in the range of 50 to less than 200 per host cell, over the course of minutes to several hours or even days, depending on the dynamics of the particular system. Phage encoded proteins produce a catastrophic disintegration of the bacterial cell in a process termed 'lysis.' Lysis disperses progeny phages into the environment where they can adsorb to new bacterial hosts and begin the process again. The phage/host relationship is very specific and in general only certain species or strains of bacteria are targeted by any one phage strain. Phages are remarkably abundant in the environment, even more so than bacteria (Srinivasiah, Bhaysar et al. 2008). This abundance is mirrored by extremely high diversity (Casjens 2008; Hatfull 2008). Phages are naturally abundant in many food products and are therefore routinely consumed. Because of their ubiquity, specificity for bacterial cells, and their lack of interaction with human, animal, or plant cells, phages have been designated by the FDA as generally regarded as safe (GRAS).

In simplest terms, application of any phage based antimicrobials can be divided into four distinct processes.
Identification of Unwanted Bacteria in the Target Process.

Assembly of one or more phage panels or multi-panels, each of which is comprised of one or more virulent phage types active against the unwanted bacterial strain(s) targeted.

Large Scale Phage Production and Processing into Application Form, and Application of the Phage Panel(s) to Control the Unwanted Bacteria in the Target Process.

1. Identification of Invasive Bacteria

The first step of the invention is to identify problem (unwanted) bacteria, in order to be able to isolate and propagate virulent phages against them.

Selection of Target Strains, Exemplified by LAB in Fuel Ethanol Fermentation Plants Many LAB phages have been identified and isolated, but most are those virulent against dairy associated LAB. While closely related, dairy and fuel ethanol fermentation LAB strains are not identical. Due to the specificity of phages, it is usually preferable that bacterial strains be used that have been isolated from fuel ethanol fermentation plants, especially those that have been demonstrated to reduce fermentation efficiencies. For example, in ethanol fermentation affected by LAB, Drs. Bischoff, Leathers, and Rich have identified 200 isolates of *Lactobacillus* species collected from commercial ethanol facilities (Skinner and Leathers 2004; Bischoff, Skinner-Nemec et al. 2007). Five example phage target strains are: *L. fermentum* 0315-1, *L. fermentum* 0315-25, *L. brevis* 84, *L. mucosae* 0315-2B, and *L. amylovorus* 0315-7B. This collection represents the more common yet genetically distinct *Lactobacillus* species isolated as contaminants from the fermenters of commercial ethanol facilities experiencing acute contamination problems. Furthermore, all but *L. amylovorus* 0315-7B have been shown to produce stuck fermentations in shake-flask models of ethanol fermentation (Bischoff, Skinner-Nemec et al. 2007). *L. fermentum* 0315-1, *L. fermentum* 0315-25, and *L. brevis* 84 were isolated from planktonic cultures, while *L. mucosae* 0315-2B and *L. amylovorus* 0315-7B were associated with biofilm cultures.

In addition to *Lactobacillus* species, other bacteria of interest include, but are not limited to, other lactic acid producing bacteria, such as species in the *Pediococcus, Lactococcus, Enterococcus, Weissella, Leuconostoc, Streptococcus*, and *Oenococcus* genera, and acetic acid producing species, such as the Acetobactor and Gluconobacter genera. Additional species of unwanted bacteria, including those affecting processes other than yeast-based fuel ethanol fermentation are also target species, and will be evident to those skilled in the art.

Sources of Bacteria

Phage are highly host specific and thus to use phage from a pre-assembled collection, the contaminating bacteria must be identified. In one permutation of the invention sufficient background information on the most commonly encountered best bacteria will be known for that specific process, as is the case for LAB and corn ethanol fermentation. Other systems, such as algal biodiesel production or cellulosic feedstock fermentation factilities, will require background analysis. Unwanted bacteria are identified by sampling the fermentation reaction at various times during the process From samples, the unwanted bacteria can be identified using genetic techniques and or isolated and characterized using classical bacteriological approaches such as morphology, physiology, and other biochemical and growth characteristics. Once background information is available for a given system, diagnosis can be made to some extent based on what is generally already known about the causes of the undesirable effects, for example LAB infection of yeast-based corn ethanol fermentation process causes stuck fermentation. From these samples, virulent bacteriophages may also be identified for target unwanted bacteria, e.g. LAB. Sufficient phages are then isolated to effectively lyse the unwanted bacteria, and an effective amount of phage solution is added to the biomass. Isolation and identification of phages is discussed in following sections.

Instead of issues being caused by single types of bacteria, multiple bacterial populations may work synergistically. Members of microbial consortia exhibiting biofilm formation activity, for example, may provide the anaerobic microenvironment required for the growth of LAB. As such, the target of phage treatment, and therefore, the target unwanted bacteria, can include not just the bacteria competing with and/or inhibiting the system reactive agents, but also any bacteria involved in forming the microenvironment required or contributing to their proliferation. Therefore, biofilm producing bacteria involved in inhibiting the system process are included in the category of targets for phage remediation. Biofilm forming genera of bacteria include *Pseudomonas* or *Vibrio* species isolated in affected systems.

Bacterial populations responsible for biofilm resulting in physical blockage in the production process may also be selected for phage treatment. All bacteria that are to be targeted for phage treatment are part of the selected bacterial subpopulation.

Laboratory Culturing of Unwanted Bacterial Strains

In one permutation of the invention, phage libraries active against the problem causing bacteria are pre-assembled as a resource to prepare active phage preparations. This requires cultivation of the problem causing bacteria. Isolation and cultivation of problem bacteria may be accomplished using traditional bacteriological approaches. For example, *Lactobacillus* species may be isolated by plating serial dilutions of the fermentation materials onto MRS (Difco Lactobacilli MRS Broth) agar plates supplemented with any chemical capable of specific inhibition of the growth of the fermentative yeast (for example, cyclohexamide may be used for this purpose). Although anaerobes, *Lactobacillus* species are aerotolerant so cultures may be set up on the bench before transferring to anaerobic or hypoxia chambers for growth. Lactobacilli may be grown in simple GasPak jars or in functional anaerobic chambers, which permit easy manipulations and assessment of anaerobic microorganisms.

2. Assembly of Phage Panel(s)

Sources of Phages

In a preferred embodiment, phage isolation to assemble the phage library is achieved through an enrichment procedure. Enrichment is an effective means for isolating new phages, as if even a single phage is present in the starting solution it is not unreasonable to obtain a final phage concentration of $10^7$ or $10^8$ plaque-forming units (PFU; corresponds to active phage particles) per ml solution (Brownell, Adams et al. 1967; Brownell and Clark 1974). As a predator, natural populations of phages are found near natural populations of their prey. Therefore, an important consideration in choosing samples is to choose them from sites where the host bacteria can be found.

The sources of phages for controlling bacterial infestations include any site where the target bacteria are commonly found. While existing phage stocks may be screened for activity on unwanted bacteria, new phages will also be isolated from the same site or location where the bacteria pose a problem, such as fermentation mash (or biomass in general), deposits in system containers, and the like.

Populations of bacterial phages will be most abundant near abundant sources of their prey. Therefore, the process of identifying phages specific for any bacterial population is to first identify an environmental site where that bacterial type is abundant. This means that there is not one environment that will serve as a source of phages for all target microbes. Instead, the exact environmental sample will vary from host strain to host strain. However, there are general guidelines for identifying the environmental sample most likely to yield desired phages. An ideal starting-point sample will often be biomass from the affected biofuel production plant. However, it is possible that the phage(s) most efficient at destroying a specific unwanted bacteria may not be those naturally co-resident with said strain(s) in the production plant. Therefore, ideal samples may also come from a production plant employing a similar process under similar conditions, or a completely different location, selected following the guidelines discussed herein. Specific physiochemical properties of the biomass are important and exact parameters will vary from host to host. An example, which is not intended to be a guideline for all protocols, would be the identification of phages active against an LAB strain. Biomass enriched in LAB is typically characterized by elevated levels of lactic and/or acetic acid. Therefore, a sample likely to possess LAB specific phages will be biomass that is fermentable, fermented, or a product of fermentation, especially LAB fermentation. Especially likely would be a fermenting material rich in sugars (the nutrient source for both the LAB and the system reactive agent, such as yeast) and with elevated levels of lactic and/or acetic acid (metabolites of LAB). Phage isolation sources may include various liquids and mash solids, obtained from biofuel production facilities of interest. In one embodiment of the invention specifically targeting LAB, fuel ethanol fermentation facilities or any fermenting feedstock may be potential sample sources. Examples include, but are not limited to, fermented dairy products, such as yogurt and cheeses such as feta, and sour foods, such as sauerkraut, pickles, kimchi, and salami as well as fermented bean curds and silage produced for livestock feed. In general, fermenting foods with a 'sour' taste indicate LAB activity, and a potential source of phages. Yogurt, for example, has been demonstrated to contain phages active against *Lactobacillus* isolates from non-dairy environments (Tao, Pavlova et al. 1997).

Phages for any given host can be found at the same conditions that are favorable to the growth of the host bacteria. Bacteria vary greatly with regard to carbon source utilization, similarly phages that infect these bacteria can be found in these environments regardless of carbon source being utilized by the bacteria. Similarly, bacteria and phages vary greatly with regard to tolerance and utilization of industrial waste materials such as metals, heavy metals, radioactivity, and toxic chemical wastes including pesticides, antibiotics, and chlorinated hydrocarbons.

As an alternative to identifying samples based on physiochemical properties, molecular tools are used to identify sediments possessing wild populations of bacteria similar to the unwanted bacteria. These methods typically require some level of purification of DNA from the environmental sample, followed by the detection of marker DNA sequences.

The most straightforward of these are polymerase chain reaction (PCR) based technologies that target 16s rDNA sequences. These can be analyzed by methods such as denaturing gradient gel electrophoreses (DGGE) or by DNA sequencing.

Laboratory Isolation of Phages

In one embodiment, the first step to identifying phages in a sample is to prepare a sterile-filtered rinsate. To do this solids and bacteria are separated by a combination of centrifugation and filtration. The rinsate, which usually has only a few individual phages against any specific host, is then supplemented with MRS media and inoculated with low levels of the specific target host. The sample is incubated for a period of overnight to several days, depending on the host growth characteristics. At this point, the liquid culture may or may not show evidence of phage activity. Chloroform may be added to 0.1% v/v in order to complete lysis of infected but un-lysed cells and phages are separated from bacterial cells and debris by centrifugation and filtration. This is the phage enrichment and may contain more than one type of phage against the target host. The presence of phages is determined by spot titering onto agar overlays containing confluent lawns of the host. It should be noted that many *Lactobacillus* species produce bacteriocins, which also produce clearings when undiluted supernatants are spotted onto lawns in agar overlays (Tao, Pavlova et al. 1997). Bacteriocins, however, are easily distinguished from phage in that they do not produce plaques following serial dilutions and are not self propagatable.

If clearings are observed, serial dilutions of the enrichment samples are plated in overlays to the point that individual, well-separated plaques are formed. To generate clonally pure phage stocks, agar plugs containing the well-separated plaques are excised from the plate and phages are eluted from the agar plugs. This process, termed plaque purification, is repeated at least one more time. At this point, the small volume (1 ml) of phages from a single plaque is considered to be clonal and the process of phage amplification can begin. Two approaches, the liquid lysate or plate lysate, approaches may be used to generate high volume, high titer lysates. In the plate lysate approach, overlays are prepared with between $10^4$ to $10^5$ PFU of phages, which produce nearly confluent lysis of the overlay. Phages are eluted from the top agar and purified by centrifugation and filtration. To prepare liquid lysates, the optimal multiplicity of infection (MOI) for maximum phage production must be first determined in a series of preliminary experiments. Then, large volume liquid lysates are prepared by inoculation with the optimal host/phage levels. After growth and lysis of the culture is observed, phages are purified by a combination of centrifugation and filtration.

In another embodiment, undesirable bacteria will be isolated from the biofuel generating culture or reaction through a method that takes advantage of cell surface recognition capacities. The most typical of these includes antibodies raised against a cell surface feature or lectins that reacte with carbohydrates. The cell surface recognition activity is then coupled to a purification methodology. Commonly used methods include biotinylation reaction to streptavidin coated beads or column matrix. The beads may be paramagnetic, relying on interaction with a strong magnetic field to separate the bacteria/antibody/biotinilation/streptavidin comples away from other materials in the sample.

Phages will be characterized minimally by host range analysis on the collection of *Lactobacillus* isolated as described above, as well as by restriction digest analysis of genomic DNA. This will provide enough information to cluster the phages into similarity groups, which may reflect host-receptor specificity. More extensive characterization may be completed if necessary or desired.

Laboratory Characterization of Efficacy of Isolated Phages

In this embodiment, once a collection of phages active against the fuel ethanol fermentation-inhibiting *Lactobacillus* strains have been assembled, the next step would be to determine efficacy of phage clearing of the hosts in batch cultures. Batch cultures are performed by inoculating liquid media with low levels of the bacterial strains of interest and incubating for a period of several days. Batch culture growth follows classic, single-step growth kinetics and can be broken down into three phases, lag, log, and stationary phase. Lag phase corresponds to the early acclimation of the inoculum to fresh growth media, log phase corresponds to the most rapid period of bacterial division, and stationary phase corresponds to the phase when limiting nutrients are depleted and cell division rates decline or cease. Bacterial growth is monitored by changes in optical density ($OD_{600nm}$). One $OD_{600nm}$ of *Lactobacillus* sp. is equivalent to approximately $5 \times 10^8 - 1 \times 10^9$ CFU/ml, where CFU=colony forming units. In the most preliminary types of phage efficacy experiments, phages are added to the bacterial culture at several different MOI (multiplicity of infection, that is the ratio of phage to host cells), typically a MOI of 0.01, 0.1, 1.0, 10.0 and if enough phages are produced, a MOI of 100. Culture ages corresponding to lag, log, and stationary phase cells are challenged with phages at each MOI. Control cultures, unchallenged by phages, is analyzed in parallel. The phage effect is typically monitored by measuring changes in host cell $OD_{600nm}$, enumerating produced phages using the overlay method, and enumerating viable host cells in the culture using the colony counting method. Care must be taken to remove free phages prior to host cell plate counting. Experiments are ideally be repeated in triplicate and quantification of individual time points performed in duplicate. Statistical comparisons of challenged and control cultures may be performed using Student's t-test (P<0.05).

Once batch culture efficacy test results are completed, the next step in this embodiment is to determine phage efficacy in a shake-flask fermentation model system containing both the fermentation yeast *Saccharomyces cerevisiae* (the system reactive agent) and the inhibitory *Lactobacillus* strains (the unwanted bacteria) (Bischoff, Liu et al. 2009). These experiments are conducted by co-culturing *S. cerevisiae* and *Lactobacillus* in a corn mash. Phages are applied at different MOI and at different times. Appropriate controls run in parallel include co-cultures not challenged with phages, yeast only cultures, and bacteria only cultures. At different time points, bacterial and phage densities are enumerated by colony and plaque counting, respectively, as described. Levels of ethanol, glucose, lactic acid, and acetic acid may be determined, for example, by high performance liquid chromatography (HPLC) using a 300 mm Aminex HPX 87H column (Bio-Rad Laboratories, Inc., Hercules, Calif.). For this, 10 ml samples are injected onto a heated column (65° C.) and eluted at 0.6 ml/min using 5 mM $H_2SO_4$ as mobile phase. Concentrations are reported as mean values (±standard deviation) of at least triplicate cultures. Statistical comparisons of challenged and control cultures may be performed using Student's t-test (P<0.05).

Assembly of Identified Phages

Once suitable phage strain(s) have been identified, phage cocktail(s), panel(s), and multi-panels may be assembled. In one embodiment, standard phage panel(s) may be assembled which are designed for use with one or more application profiles, including, but not limited to: certain feedstocks, environments, production processes, fuel products, system reactive agents, or geographical locales. These pre-assembled phage panel(s) may be stored as a sort of 'phage library' that can be stored onsite or offsite (e.g. at a central laboratory/manufacturer) and accessed for rapid response to infestations. In another embodiment, standard phage panel(s) may be custom assembled for a particular situation. In a preferred embodiment, these approaches may be used in conjunction. For example, a standard phage panel(s) may be utilized for rapid response, and then replaced/combined with a more specific custom phage panel(s) once it is prepared.

3. Production of Phage Panel(s)

Proliferation of Isolated Phages

Once suitable phages are isolated and phage cocktail(s), panel(s), and/or multi-panels assembled, they generally will be proliferated to produce a suitable quantity for biomass treatment, and processed as required for the desired application or destination. This may be accomplished onsite at the biofuel facility, or offsite at an external lab or production facility with the resulting quantities of phage panel(s) packaged, stored, and/or shipped as needed. Phages can be stored in liquid buffers at 4° C., deep frozen (with proper cryoprotectant) at −80° C., freeze dried (with protectant). The survival rate of phage stock should be examined periodically, and the optimal storage conditions have to be optimized. Phages may be suspended in a medium suitable for application, such as a substance that adheres to vessel walls for use in treatment of process vessels. The solution containing the phages may be filtered to concentrate and/or isolate the assembly of phages. Phages may also be encapsulated with a water-soluble coating. This allows phage cocktails, panels, and multi-panels to be shipped to remote locations for use, and allows the manufacture to be made at optimized central locations. While, in the preferred embodiment, the phage panel(s) are produced "on location," it is sometimes preferred that the manufacture of large volumes of phage panel be centralized in locations where the necessary equipment and resources are readily available. Alternatively, phage panel(s) may be processed for storage before proliferation.

A preferred embodiment of the invention is illustrated in FIG. 1. Valve 116 releases unwanted bacteria from storage tank 105 into phage concentration tank 102. Valve 117 releases growth media from storage tank 106 to feed the unwanted bacteria and allow them to replicate and proliferate. Valve 115 releases phage panel(s) from storage tank 104. The phages then infect the unwanted bacteria in the concentration tank and reproduce. The resulting mixture is delivered to the reactor or into storage tank 103. A portion of the mixture may be recycled back into the phage concentration tank to provide a continuous supply of virulent phages. Residence time and recycle ratio may be adjusted to control the concentration of phages in the phage concentration tank. This assembly and process may be referred to as a 'phage proliferator/concentrator,' and may be used either onsite or offsite.

As an alternative to supplying unwanted bacteria, biomass from the reactor, 101, may be cycled through the continuous phage concentration system. In FIG. 1, this is depicted as biomass flowing through valve 118 and 112 into phage concentration tank 102, and some portion of the contents of the phage concentration tank being diverted by valve 113 back into the reactor, 101. The unwanted bacteria resident in the fermenting biomass will act as hosts for the virulent phages to infect, reproducing the virulent phages. In an alternative embodiment, the biomass is passed through a filtration process (such as one or more filters to remove debris and "trash", followed by a microfiltration tangential flow filter to separate bacteria and phages) to separate the bacteria resident in the biomass from phages and/or other organisms and agents.

Isolation and Proliferation of Resident Phages

Alternatively, phages can be produced without identification by simply proliferating resident phages directly from the target biofuel production process. One embodiment of this aspect of the invention is also described in FIG. 1. Biomass stream is diverted from reactor 101 through valves 118 and 112 into phage concentration tank 102. A suitable growth media is added from tank 106 to cause proliferation of the unwanted bacteria and an additional chemical is included to prevent growth of the fermentative eukaryote, for example cyclohexamide. This allows for the preferential culture of the contaminating bacteria over the fermentative microorganism. As the unwanted bacteria concentration rises, phages present in the biomass stream will infect the unwanted bacteria and reproduce, increasing the quantity and concentration of phages virulent for the unwanted bacteria.

In an alternative embodiment, the phages may be isolated from any portion of the biomass stream (not just biomass taken from the bioreactor). Some portion of the biomass may be taken before the biomass enters the reactor, after it leaves the reactor, or any other part of the biofuel production system. So long as the biomass contains phages virulent for at least some of the unwanted bacteria, it may be used. In another embodiment, phages applied to the biomass (for example, from a standard phage panel), and phages that are a result of applied phages (for example, progeny of applied phages), may be recaptured and used as resident phages as described herein.

Proliferating resident phages without isolation provides a number of benefits. Because the unwanted bacterial strain(s) need not be identified, time and expense is saved. As resident phages normally exist alongside their host bacteria, if the unwanted bacteria change over time, the proliferated phages will also change, because the system simply proliferates and increases the concentration of the phages already present. This is especially useful because of the dynamic nature of microorganism populations—that is, as the concentration of the originally targeted unwanted bacterial strain(s) is reduced, it is possible and even likely that other strain(s) will be free to increase in concentration. In this embodiment, the treatment, therefore, is also dynamic: as the bacterial populations shift, so does the phage panel(s). For this reason, it may be termed a 'dynamic phage multi-panel'.

Purification of Dynamic Phage Multi Panel

In an alternative embodiment, the dynamic phage multi-panel is purified and optionally concentrated before proliferation and/or application to the biomass stream. In this embodiment, the multi-panel is passed through a filtration system (such as one or more filters to remove debris and "trash", followed by a microfiltration tangential flow filter to separate bacteria and phages), to isolate the phages from the remainder of the biomass. Optionally, the multi-panel may also be concentrated, such as by an ultra-filtration tangential flow filter. These steps may be performed before proliferation or before application, although prior to proliferation is preferred for more efficient utilization of filters. This embodiment may be useful in situations where it is desirable to prevent the inadvertent proliferation of microorganisms or agents that may be harmful to the biofuel process or reaction.

Dynamic Phage Multi-panel in Conjunction with a Standard Phage Panel(s)

The dynamic phage multi-panel can be used in place of or in conjunction with the standard phage panel(s) described previously. In a particular embodiment of the invention, a pre-assembled standard phage panel(s) may be used to respond rapidly to an infestation, while the dynamic phage multi-panel is setup and production increased to a suitable output and concentration. In another embodiment, a custom-assembled standard phage panel(s) would be used in conjunction with the dynamic phage multi-panel. The custom-assembled standard panel(s) would specifically target the identified unwanted bacteria, ensuring therapy was focused on those species, while the dynamic multi-panel would serve to both a) reduce the quantity of custom-assembled panel necessary by virtue of producing some level of phages targeting the same bacteria and b) hold in check other, non-identified or non-targeted species as described previously.

4. Examples

A set of experiments were conducted to illustrate the ability to identify and reduce the level of unwanted LAB bacteria in fermentation system processing corn mash to ethanol.

Example 1

A Series of LAB strains were isolated from biofuel ethanol fermentation plants. Of a total of 18 samples obtained from two commercial biofuel ethanol fermentation plants two were chosen for study of effects upon acid production that was disruptive to ethanol production—Fermenter samples after 11 hours and after 24 hours from Plant A. Dilution series of either 1 ml of each liquid and solid sample (following elution of bacteria from 1 gm of solid material into 10 ml of PBS) were prepared in sterile phosphate buffered saline solution and spread onto MRS plate. The plates were incubated anaerobically.

To isolate clonally pure LAB, well-separated colonies were picked and subject to several rounds of colony purification. The identity of select purified isolates were determined based on comparing the 16s rRNA coding region to sequences in the public database. This was accomplished by isolating DNA from a colony, PCR amplification of the 16s rRNA coding region, followed by purification and BigDye terminator sequencing the PCR product. All isolated bacteria were determined to be lactic acid bacteria, including *Streptococcus equinus, Enterococcus* sp., *Bifidobacterium thermophilum, Pediococcus pentosaceus, Lactobacillus plantarum, L. mucosae, L. coryniformis*, and *L. fermentum*.

Because comparably few bacterial species actually grow in culture, culture based bacterial identification methods do not in fact provide an accurate portrait of bacterial species from most samples. Therefore, in addition to determining the identification of bacteria cultured from the fermentation plant samples, a culture-independent approach was used to evaluate the population of bacteria at the plant. This approach was based on shotgun pyrosequencing of bacterial 16s rRNA coding region PCR products. Total DNA isolated from two samples were processed: the 11 hour and 24 hour Fermenter samples from Plant A, the 16s coding region amplified by PCR, and subject to bacterial tag-encoded FLX amplicon pyrosequencing (bTEFAP). Resulting sequences were trimmed and quality scored. All sequences passing quality score were compared using BLASTn to a ribosomal database to make taxonomic classifications.

A total of 37,397 bacteria were assayed corresponding to 10,209 and 27,188 individual bacteria from the 11 hr and 24 hr samples, respectively. These bacteria could be organized into sequence clusters, or operational taxonomic units, which correlate to the number of species. A total for 120 different species were identified in the two samples, 70 species in the 11 hr sample and 100 species in the 24 hr sample (Table 5). Only 30 species were found in both samples. 108 species were categorized as "low abundance", e.g. less than 100 individuals for each sample. The 12 most abundant species were found in both samples and constituted 95% and 97% of all the bacteria identified in the 12 hr and 24 hr samples, respectively. Seven of the thirteen species were *Lactobacillus* species, including *Lactobacillus fermentum*, *L. johnsonii*, *L. mucosae*, *L. reuteri*, *L. rhamnosus*, and *L. vaginalis*. The other bacteria identified as the most abundant bacteria are not known to be acid producing and as such are not considered to be problematic.

TABLE 1

Culture independent analysis of the thirteen most abundant bacterial species present in Plant A samples 7 hour and 24 hour.

| Species | 7 HR, % | 24 HR, % | 7 HR, counts | 24 HR, counts |
|---|---|---|---|---|
| *Aquimarina* sp | 67.7 | 39.7 | 6916 | 10791 |
| *Pseudomonas* sp | 23.0 | 16.1 | 2343 | 4384 |
| *Lactobacillus mucosae* | 0.8 | 18.8 | 86 | 5107 |
| *Lactobacillus reuteri* | 0.6 | 13.0 | 57 | 3538 |
| *Lactobacillus* sp | 1.6 | 4.4 | 159 | 1189 |
| *Lactobacillus johnsonii* | 0.1 | 2.9 | 12 | 799 |
| *Caloramator* sp | 0.7 | 0.5 | 75 | 135 |
| *Lactobacillus vaginalis* | 0.1 | 0.6 | 11 | 160 |
| *Lactobacillus fermentum* | 0.0 | 0.5 | 3 | 148 |
| *Prevotella* sp | 0.3 | 0.4 | 26 | 118 |
| *Alkaliflexus* sp | 0.9 | 0.1 | 89 | 31 |
| *Lactobacillus rhamnosus* | 0.1 | 0.3 | 15 | 91 |
| total | 95.9 | 97.4 | 10,209 | 27,188 |

Shown is the % of population and the actual number of sequence reads corresponding to that species (counts).

Importantly, the identification of *Lactobacillus* species as the numerically dominant acid producing bacteria in these fermentation samples strongly supports the contention that *Lactobacillus* is a critical genera to target by phage application.

Example 2

With the successful collection of phages as described in Example 1 active against the biofuel ethanol fermentation-inhibiting *Lactobacillus* strains, experiments designed to test the efficacy of phage in controlling LAB were conducted. Batch culture growth follows classic, single-step growth kinetics and can be broken down into three phases, lag, log, and stationary phase. Lag phase corresponds to the early, acclimation of the inoculum to fresh growth media, log (logarithmic or exponential) phase corresponds to the period of most rapid bacterial cell division, and stationary phase corresponds to when limiting nutrients are depleted and cell division rates decline or cease. Bacterial growth was monitored by changes in optical density ($OD_{600nm}$) with $OD_{600nm}=1$ of *Lactobacillus* sp. corresponding to approximately $1\times10^8$ cfu/ml (cfu=colony forming units, a measurement of the number of viable cells).

The LAB control experiment was conducted using host *L. fermentum* strain 0315-25 and four phages (25Soila, 25Sau, 25Wang, and 25Komiso). Nine parallel cultures were set up. All nine cultures received the same bacterial inoculum and incubated at 37° C. until early-mid log growth phase. At this point, phage was added either singly or combined into phage cocktails. The multiplicity of infection (moi, or the ratio of phage to bacterial cells) was adjusted to 0.1, 1, 5 or 10. Bacterial growth was monitored for 27 hours to measure the effect of the phage treatment. The nine cultures were incubated until the culture $OD_{600}$ had increased from the initial inoculum of less than 0.1 to around 0.5, at which time 8 of the nine cultures received phage lysate and the ninth, control culture was treated with an equal volume of MRS broth. Due to dilution, there was an immediate drop in the $OD_{600}$ of all nine cultures to about 0.3. However, within minutes after the addition of phage, the control culture was showing signs of recovery while the phage treated cultures did not. By 15 minutes after addition of phage at moi of 5 or 10, the culture $OD_{600}$ dropped to below the detection limit. The cultures treated with the lower phage moi of 0.1 and 1 also exhibited a drop in $OD_{600}$ to below the detection limit, although the process took between 5 and 10 hours. At the end of the testing period, the control culture reached stationary stage at an $OD_{600}$ between 1.0 and 1.2, while all of the phage treated cultures remained "clear", with $OD_{600} \leq 0.000$, at 27 hours following treatment.

The batch culture phage efficacy test clearly demonstrated that phage treatment controlled bacterial growth for at least 27 hours. Because phage were demonstrated to control bacterial growth in pure culture, experiments testing the capacity of this phage preparation to control bacterial growth in a mixed culture with the fermentative yeast were conducted.

Example 2

Another experiment was conducted to determine phage efficacy on controlling LAB in a shake-flask fermentation contamination model system (Bischoff et al., 2009). For each experiment, five shake-flask cultures were set up with a corn mash feedstock inoculated with *Saccharomyces cerevisiae* to an initial $OD_{600}=1$. Four of the *S. cerevisiae* cultures were contaminated with *L. fermentum* 0315-25 at a density of $10^7$ cfu/ml (yeast+LAB). Three of the LAB contaminated yeast cultures were treated with phages 25Sau and 25Inf, either singly or in combination, at moi of 1, 20, and 0.5 and 10, respectively. The entire experiment was set up in triplicate and the data are reported as the mean value±SEM for triplicate cultures (Table 2).

TABLE 2

LAB phage efficacy trial in a fermentation contamination model system.

| | Ethanol | Glucose | Lactic Acid | Acetic Acid |
|---|---|---|---|---|
| A. Yeast | 137 +/− 2.4 | 0.44 +/− 0.19 | 1.9 +/− 0.05 | 0.85 +/− 0.04 |
| B. Yeast + LAB | 117 +/− 1.6 | 28.7 +/− 5.7 | 5.3 +/− 0.13 | 2.8 +/− 0.07 |
| C. Yeast + Lab + Phage Sau | 137 +/− 1.0 | 0.47 +/− 0.13 | 2.4 +/− 0.01 | 0.76 +/− 0.03 |
| D. Yeast + Lab + Phage Inf | 134 +/− 0.9 | 0.42 +/− 0.13 | 2.4 +/− 0.07 | 0.84 +/− 0.03 |
| E. Yeast + Lab + Phage Sau + Inf | 136 +/− 0.9 | 0.60 +/− 0.09 | 2.4 +/− 0.04 | 0.76 +/− 0.03 |

For Table 2, the amount of ethanol, glucose, lactic acid, and acetic acid were determined at the end of a 72 hour fermentation in corn mash with *S. cerevisiae* only (Fermentation control, A.), *S. cerevisiae* and LAB co-culture (Contamination control, B.), or the *S. cerevisiae* and LAB co-culture treated with phage 25Sau (C.), 25Inf (purple), individually or 25Sau+25Inf together (D.). Values are in g/L and are the average of triplicate experiments, with the indicated standard deviations.

The effect of phage treatment compared to no treatment was determined by measuring levels of ethanol, glucose, lactic acid, and acetic acid were determined after 72 hours of incubation. These measurements were made using high performance liquid chromatography (HPLC) using a 300 mm Aminex HPX 87H column (Bio-Rad Laboratories, Inc., Hercules, Calif.) using 10 ml of sample injected onto a heated column (65° C.) and eluted at 0.6 ml/min using 5 mM $H_2SO_4$ as mobile phase. Concentrations were reported as mean values (±standard deviation) of triplicate cultures. Statistical comparisons of challenged and control cultures were performed using Student's t-test (P<0.05) (FIG. 5). The concentration of phage was analyzed at three times during the experiment: at 7, 18, and 24 hours and found to vary between $10^5$ and $10^8$ pfu/ml. The fermentation model experiment was also conducted using a lower initial inoculum of LAB and phage at $10^6$ cfu/ml. The lower LAB inoculum level did not inhibit ethanol production to the extent that the $10^7$ inoculum level did, however the phage treatments recovered ethanol yields to the same level as the uncontaminated yeast culture.

The fermentation model clearly demonstrated the capacity that phage have to prevent ethanol yield loss in the presence of *Lactobacillus*.

5. Application of Phage Panel(s)

Application of the phage panel(s) for control of the unwanted bacteria is accomplished in a variety of ways, four of which are described below. These are: 1) pre-loading of the biomass stream before reaction, 2) continuous treatment of the reacting biomass for prevention purposes or for treatment of chronic bacterial infestations, 3) acute treatment of the reacting biomass for sudden bacterial overgrowth, and 4) treatment of an empty reactor before reaction begins. These four methods may be combined in any combination, as necessary for the particular plant and application and use of the invention.

1) Pre-loading

In this aspect of the invention, referring to FIG. 1, the incoming biomass stream 181 is pre-treated before it enters reactor 101. Three-way valve 111 diverts some or the entire incoming biomass stream through phage treatment/concentration vessel 102. After incubation for a suitable time, as described below, the treated biomass flows through valve 113 into the reactor. This pretreatment of the biomass stream before it enters the reactor 'pre-loads' the biomass stream with phages, allowing the phages to begin adsorption and infection of the bacteria before the reaction process begins.

If insufficient bacteria are present for the infection rate to be significant, the phages will remain in the now-reacting biomass. If concentrations of unwanted bacteria are low, the infection rate will also be extremely low, but the few infections that do occur will only increase the number of phages present. With a large quantity of phages residing in the reacting biomass, rising concentrations of bacteria will result in rising infection rates and, thus, rising phage concentrations, thereby preventing an acute infection—before production efficiency is negatively impacted.

2) Continuous Treatment

In another aspect of the invention, the biomass residing in reactor 101 is treated continuously. Some portion of the volume of the reactor flows through valves 111 and 112 into phage treatment/concentration vessel 102. After incubation for a suitable time, as described below, the treated biomass flows through valve 113 into the reactor. Alternatively, concentrated phage mixture may be delivered directly to the reactor from phage concentration/treatment vessel 102 (through valve 113) and/or phage storage tank 103 (through valve 119).

Continuous treatment of the reacting biomass can be used to 1) address chronic infections of the reaction process, and 2) prevent infection, such as in plants that regularly deal with sudden, acute overgrowths. The rationale for 'pre-treating' the biomass is detailed in the preceding section. Continuous treatment is a natural extension of 'pre-loading' the biomass stream, such as in situations in which pre-loading was not entirely sufficient in itself to provide a suitable concentration of phages, or in which phage concentration is decreasing due to increasing volume.

3) Acute Treatment

In another aspect of the invention, the reacting biomass is treated with a sufficient quantity of phages to rapidly increase phage concentration. A large dose of concentrated phage solution is delivered to reactor 101 from storage tank 103 (through valve 119) and/or from the phage concentration/treatment tank 102 (through valve 113). To provide the quantity necessary, the phage treatment may be supplemented by adding phages from an external location, possibly delivered in a concentrated liquid or dried form, as discussed previously.

Alternatively, the process described above for continuous treatment may be modified to treat all, or at least a greater portion, of the reacting biomass by increasing the percentage of the reacting biomass that is circulated through the phage treatment/concentration tank, or by adding multiple treatment tanks. Multiple concentration/treatment tanks may also be used in other aspects of application, concentration, or proliferation in order to increase biomass treatment and phage production capacity.

Delivering a large quantity of phages to the reacting biomass can be used to treat the acute bacterial overgrowths responsible for substantially retarded reactions, such as 'stuck' fermentations. Rapid increase of phage concentrations in biomass with a large concentration of unwanted bacteria will cause rapid infection and lysis of the unwanted bacteria. As the lytic cycle completes, the phage concentrations will increase as the bacterial concentrations decrease, until the bacteria population is reduced to acceptable levels and the reaction process can proceed without interference.

4) Equipment Treatment

In another aspect of the invention, concentrated phage mixture in a liquid form is used to treat plant equipment. One embodiment of this aspect is depicted in FIG. 1, where phage panel(s) from tank 104 (through valve 115), or concentrated phage mixture from phage treatment/concentration tank 102 (through valve 113) or storage tank 103 (through valve 119), is delivered into fermentation tank 101. The mixture is left to incubate for a period sufficient for infection and lysis of unwanted bacteria, and flushed to waste or returned to a storage tank or the phage proliferation tank. Methods to reduce the quantity of phages needed for treating equipment may include spraying the phage mixture onto the inner tank walls rather than completely filling the tank, and/or suspending the phages in a medium that will cause them to remain on the tank and equipment.

Phage treatment of plant equipment, particularly the reactor, pipelines, and related equipment, will reduce unwanted bacteria levels residing on or in the equipment. The equipment may be treated between every reaction batch, or on a schedule based on time, number of batches processed, or volume of biomass processed. Regular treatment will prevent the buildup of unwanted bacteria and the infestation of new batches with unwanted bacteria from previous batches, especially if coupled with a regular regimen of mechanical cleaning. Alternatively, if a continuous production scheme is used (as opposed to batch production), phage treatment may be incorporated into a regular preventative cleaning schedule, or as part of a cleaning/disinfection process after serious bacterial infestations.

Incubation of Phage Solution

In the phage concentration tank and in any treatment applications, the phage panel(s)/mixture must have a residence time sufficient for the phages to progress to the desired stage of the lytic cycle. Treatment is not complete until the lytic cycle is complete—starting with adsorption (initial attachment) of the phages to the bacteria, progressing through infection of the bacteria and replication of the phages, and ending with lysis of the bacterial cells. In some cases, the phage mixture must reside at the point of application until the entire cycle is completed. This is the case for treatment of an empty tank, as described above.

In some cases, however, residence time of the biomass at the point of application need only be sufficient for adsorption and firm attachment of the phages to the bacteria. This would be the case in the phage concentration tank (102 in FIG. 1). Once the phages have attached to the bacteria, the lytic cycle will progress to completion regardless of the location. As long as a sufficient portion of the contents of the phage concentration tank are recycled so that the tank is replenished with phages and, if desired, the concentration is rising, there is no need for the mixture to reside in the tank for the entire lytic cycle. This process will reduce residence time, thereby increasing throughput and process efficiency.

During treatment (i.e. some or all of the biomass stream passes through a phage treatment tank, whether before or after entering the reactor, and then passes into the reactor), releasing the treated biomass back into the reactor before the lytic cycle completes will cause the infected bacteria to burst inside the treatment tank. This will result in a type of continuous treatment, as described in the relevant section above.

Alternatively, a separate treatment tank(s) may be used. The treatment tank would be supplied with concentrated phage mixture from either the phage concentrated tank or from an outside source of phages, and biomass would be passed through the treatment tank. A separate treatment tank would allow the phage concentrator to be operated at a rate independent of the treatment flow rate required.

Suitable Concentration Levels of Bacteria and Phages

The simple fact that phages virulent for a certain bacteria are present at any given concentration (where phage concentrations are measured in 'plaque forming units,' or (PFU) does not mean that they will necessarily be effective at reducing bacterial concentrations (where bacterial concentrations are measured in 'colony forming units,' or (CFU) at that phage concentration. Like most predators, phages are designed to proliferate alongside their host, without completely destroying their host population. Therefore, unlike most antibiotics and other chemicals, increasing phage concentration levels does not necessarily correspond to increased efficacy or even increased destruction of bacteria.

In general, however, a MOI (ratio of infectious agents—phages—to infection targets—targeted bacteria), on the order of one (1) is considered effective, with ten to ten-thousand (10-10,000) being preferred. In the case of LAB in corn ethanol yeast-based fermentation, concentrations of bacteria from $10^5$ to $10^9$ CFU/mL have been shown to have significant negative impact on ethanol production, and concentrations of phages between $10^4$ and $10^9$ PFU/mL are considered feasible to produce when dealing with LAB virulent phages, with $10^6$ to $10^9$ PFU/mL being preferred for increased reaction rates.

Therefore, in one embodiment of this invention, the phage panel(s) application methods described previously apply phages such that the target MOI at the point of treatment is at least one (1), with at least ten (10) being preferred and at least one hundred (100) being especially preferred.

In a preferred embodiment, the invention is focused on controlling LAB in yeast-based corn ethanol fermentation, and the phage panel(s) application methods described previously apply the panel(s) at concentrations of at least $10^4$ PFU/mL, with at least $10^5$ PFU/mL being preferred, and $10^6$ PFU/mL being especially preferred.

Concentration of Unwanted Bacteria in Reacting Biomass

It may be necessary at times to increase the rate of phage adsorption and infection of the unwanted bacteria. This may occur when the concentration of unwanted bacteria are high enough to reduce efficiency, but low enough that adsorption and infection is occurring at an insufficient rate, as discussed above. This can be accomplished by increasing the concentration of phages at the point of application. If phage production is dependent on the concentration of bacteria present in the biomass, however, it may not be possible to produce a sufficient quantity of phages at a rate sufficient for treatment. Therefore, it is desirable in some situations to increase the concentration of bacteria in the biomass in order to increase phage proliferation.

Figure 2:
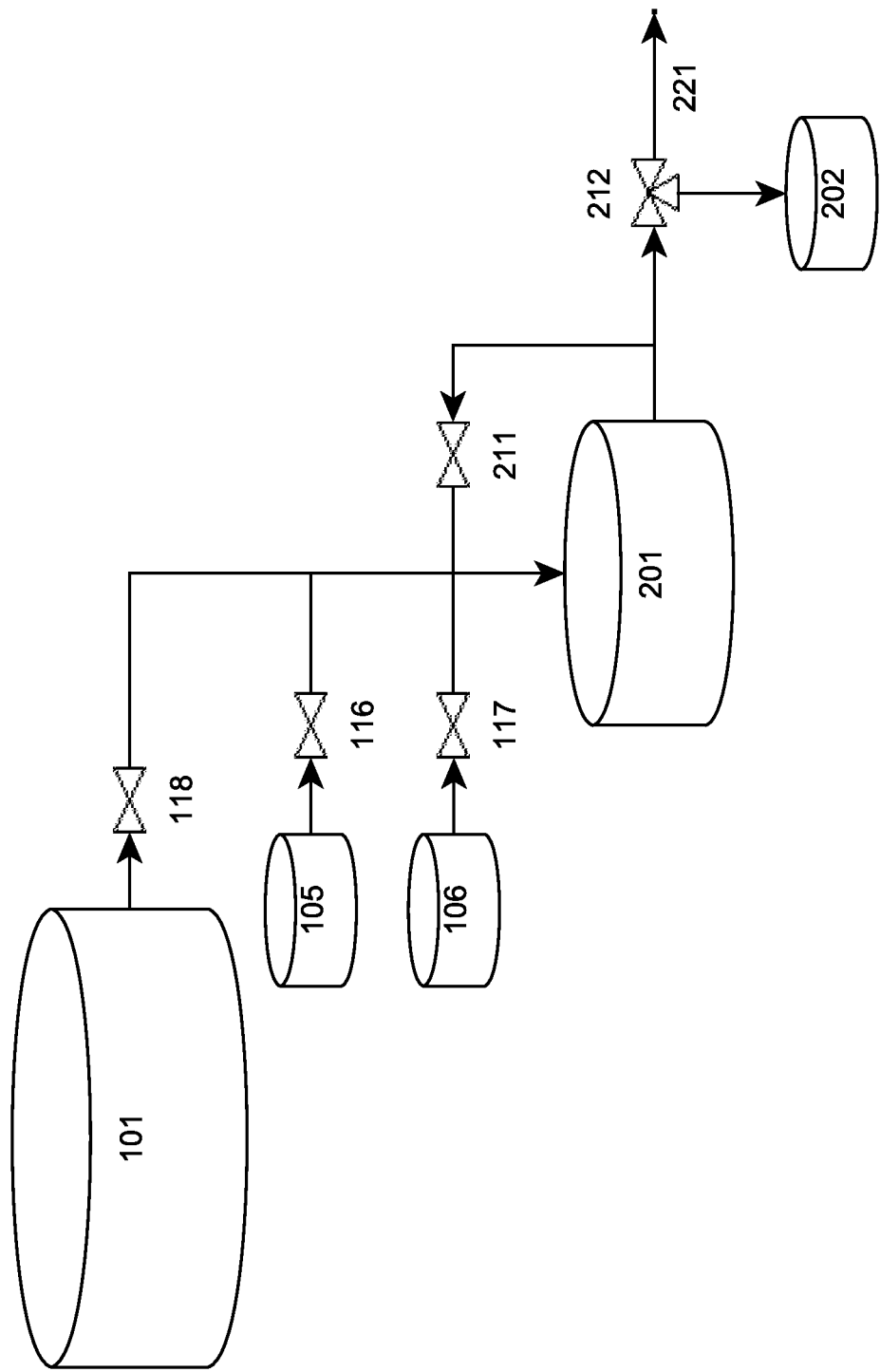
FIG. 2 is a diagrammatic representation of one aspect of the method of the invention.

In another aspect of the invention, therefore, a continuous bacteria concentration/proliferation system is included in the system described above. An embodiment of this aspect is in FIG. 2. Reacting (for example, fermenting) biomass from reactor 101 is fed into bacteria proliferation/concentration tank 201 through valve 118. Initial bacteria may be supplied from storage tank 105 through valve 116. Growth media suitable for the unwanted bacteria, such as MRS or Rogosa SL media for Lactobacilli species, is added to the bacteria proliferation/concentration tank from tank 106 through valve 117. Valve 212 directs the flow from the bacteria proliferation/concentration tank to a storage tank 202 and/or through conduit 221 to the phage proliferation/treatment system. A portion of the outflow is recycled through valve 211 back into the bacteria proliferation/concentration tank to continue the bacteria proliferation process and to increase the concentration of bacteria in the tank. Residence time in tank 201 is adjusted for the specific strain(s) of unwanted bacteria to maximize proliferation.

Alternatively, the concentration of the unwanted bacteria in the treatment tank may be rapidly increased by adding unwanted bacteria directly from a storage vessel (such as tank 105 in FIGS. 1 and 2) or a bacteria proliferation/concentration vessel (such as tank 201 in FIG. 2), to the application point, for example, a phage proliferation/concentration vessel (such as tank 102 in FIG. 1) or a separate treatment vessel. Although this appears to be counterintuitive, the goal is to raise the concentration of unwanted bacteria at the point of application to a level sufficient for the infection rate of the unwanted bacteria by the phages to increase to a level sufficient for treatment. As the treatment continues, the concentration of phages will increase as more host bacteria are infected, used to reproduce phages, and lysed. Conversely, the concentration of bacteria will decrease to levels below that at the beginning of treatment, and below that at which the unwanted bacteria are interfering with the reaction process.

Monitoring Unwanted Bacteria

It is desirable to monitor the levels of unwanted bacteria before, during, and after application of phage panel(s) in order to maximize treatment efficacy and efficiency. Therefore, an embodiment of the invention incorporates one or more means to monitor the presence and/or concentration (absolute or relative) of target unwanted bacteria. Suitable means include, but are not limited to: taking biomass samples at regular intervals, and using standard microbiological techniques and/or DNA based molecular techniques in an on- or off-site laboratory; utilizing 'rapid field assays,' such as those offered by ETS Labs; or monitoring of levels of known metabolites, such as lactic or acetic acid.

In a preferred embodiment, a yeast-based fuel ethanol fermentation system uses a combination monitoring approach comprised of: constant or frequent monitoring of lactic and/or acetic acid levels, regular usage of rapid field assays, with occasional laboratory analysis of samples. This multi-faceted approach provides a combination of the feasibility and shorter lag-times of rapid monitoring techniques (metabolites and field assays) with the greater accuracy and precision of laboratory analysis. Thus, this embodiment provides both rapid monitoring of daily conditions and fluctuations, and monitoring for additional longer-term problems and warnings, and the treatment program may be adjusted accordingly.

Application in Conjunction with Other Control Methods

In an embodiment of this invention, phages are applied in conjunction with one or more other means of controlling unwanted bacteria, such as antibiotic, biocide, or antimicrobial therapies. In this embodiment, phage treatment can be applied at alternating times with the selected additional treatment(s), in phases (e.g. initial treatment with phages and follow up treatment with antibiotics, or vice versa), or simultaneously. Such treatment options may be desirable, for example, during phage production when the phages produced are not yet sufficient for sole therapy; or when antibiotic therapy is still desired, but phage therapy is employed on a rotational basis to reduce antibiotic usage and development of resistance to antibiotics. Selection of suitable therapies and combinations thereof is well within the abilities of one of ordinary skill in the art of microbiology and biological industrial process management.

Another Preferred Embodiment

In a preferred embodiment of the invention described, the bioreaction is a fermentation process for the production of fuel, the bioreactor is a tank (and any related apparatuses or assemblies) used in industrial fermentation, and the biomass is a feedstock, or any downstream, processed portion of the original feedstock. In an especially preferred embodiment, the invention is applied specifically to ethanol production. The feedstock in this embodiment may be any feedstock suitable for fermentation (before, during, or after any additional treatment steps) in the process of producing ethanol. Suitable feedstocks include, but are not limited to both sugar/starch and cellulosic/lignocellulosic feedstocks: grains (such as corn, wheat, milo, barley, millet), sugar cane, sugar beets, molasses, whey, potatoes, agricultural residue (crop residues such as bagasse, wheat straw and corn stalks, leaves, and husks), forestry residue (logging and mill residues such as wood chips, sawdust, and pulping liquor), grasses (hardy, fast-growing grasses such as switchgrass grown specifically for ethanol production), municipal and other wastes (plant-derived wastes such as household garbage, paper products, paper pulp, and food-processing waste), and trees (fast-growing trees such as poplar and willow grown specifically for ethanol production) (http://www.afdc.energy.gov/afdc/ethanol/feedstocks.html); however, grain, sugar cane, and sugar beet feedstocks are preferred, with corn feedstock being especially preferred.

Deactivation of Phages

Once the biomass stream has passed beyond the process requiring phage treatment, the phages are no longer needed. In most applications, the biomass stream may simply continue down the process flow without further treatment. For instance, in fuel ethanol production, the distillation process will denature phages resident in the biomass, while many of the phages will settle out in the waste sludge. In most cases, the concentration of the phages in the waste streams will not be significantly higher than that of biomass streams which have not undergone phage treatments. Additionally, since phages are highly host-specific, they do not pose a significant health risk to wildlife or human populations coming in contact with them, as is recognized by the GRAS classification of phages by the FDA.

In some cases, however, it may be desirable to reduce the concentration of the phage panel(s) in the biomass stream after treatment. Depending on the phage(s) employed, this may be performed, for example, by a strong denaturing agent (such as sodium hypochlorite), a strong acid, a strong base, or even heat. Therefore, an embodiment of this invention incorporates one or more means of denaturing the phage panel(s) employed. Suitable means may include, but are not limited to: application of a sufficient concentration of denaturing agent, acid, or base to all or some portion of the biomass stream or heating of all or some portion of the biomass stream to a sufficient temperature to denature the phages utilized. The specific parameters will vary largely depending on the phage strain(s) comprising the phage panel(s) employed, and are well within the skill of one skilled in the art of microbiology.

Scope of the Invention

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

REFERENCES

Ackermann, H. W. (2007). "5500 Phages examined in the electron microscope." *Arch Virol* 152(2): 227-43.

Bischoff, K. M., S. Liu, et al. (2009). "Modeling bacterial contamination of fuel ethanol fermentation." *Biotechnol Bioeng* 103(1): 117-22.

Bischoff, K. M., K. A. Skinner-Nemec, et al. (2007). "Antimicrobial susceptibility of *Lactobacillus* species isolated from commercial ethanol plants." *J Ind Microbiol Biotechnol* 34(11): 739-44.

Bren, L. (2007). "Bacteria-Eating Virus Approved as Food Additive." *FDA Consumer magazine* 41(1).

Brownell, G. H., J. N. Adams, et al. (1967). "Growth and characterization of nocardiophages for *Nocardia canicruria* and *Nocardia erythropolis* mating types." *J Gen Microbiol* 47(2): 247-56.

Brownell, G. H. and J. E. Clark (1974). "Host range alteration of nocardiophage phi C following lysogenization of Nocardia erythrypolis." *J Gen Virol* 23(3): 247-54.

Brussow, H. (2001). "Phages of dairy bacteria." *Annu Rev Microbiol* 55: 283-303.

Casjens, S. R. (2008). "Diversity among the tailed-bacteriophages that infect the Enterobacteriaceae." *Res Microbiol* 159(5): 340-8.

De Alwis, H. and D. N. Heller "Multiclass, multiresidue method for the detection of antibiotic residues in distillers grains by liquid chromatography and ion trap tandem mass spectrometry." *J Chromatogr A* 1217(18): 3076-84.

Hatfull, G. F. (2008). "Bacteriophage genomics." *Curr Opin Microbiol* 11(5): 447-53.

Housby, J. N. and N. H. Mann (2009). "Phage therapy." *Drug Discov Today* 14(11-12): 536-40.

Jones, D. T., M. Shirley, et al. (2000). "Bacteriophage infections in the industrial acetone butanol (AB) fermentation process." *J Mol Microbiol Biotechnol* 2(1): 21-6.

Kropinski, A. M. (2006). "Phage Therapy—Everything Old is New Again." *Can J Infect Dis Med Microbiol* 17(5): 297-306.

Makanjuola, D., A. Tymon, et al. (1992). "Some effects of lactic acid bacteria on laboratory-scale yeast fermentation." *Enzyme Microbial Technol* (14): 350-357.

Mattey, M. and J. Spencer (2008). "Bacteriophage therapy—cooked goose or *phoenix* rising?" *Curr Opin Biotechnol* 19(6): 608-12.

Mc Grath, S., G. F. Fitzgerald, et al. (2007). "Bacteriophages in dairy products: pros and cons." *Biotechnol J* 2(4): 450-5.

Narendranath, N. (2003). Bacterial contamination and control in ethanol production. *The Alcohol Textbook*. K. A. Jaques, T. P. Lyons and D. R. Kelsall. Nottingham, UK, Nottingham University Press: 287-298.

Narendranath, N. V., S. H. Hynes, et al. (1997). "Effects of lactobacilli on yeast-catalyzed ethanol fermentations." *Appl Environ Microbiol* 63(11): 4158-63.

Sabour, P. M. and M. W. Griffiths (2010). *Bacteriophages in the Control of Food- and Waterborne Pathogens*, ASM Press.

Schell, D. J., N. Dowe, et al. (2007). "Contaminant occurrence, identification and control in a pilot-scale corn fiber to ethanol conversion process." *Bioresour Technol* 98(15): 2942-8.

Skinner, K. A. and T. D. Leathers (2004). "Bacterial contaminants of fuel ethanol production." *J Ind Microbiol Biotechnol* 31(9): 401-8.

Srinivasiah, S., J. Bhaysar, et al. (2008). "Phages across the biosphere: contrasts of viruses in soil and aquatic environments." *Res Microbiol* 159(5): 349-57.

Sturino, J. M. and T. R. Klaenhammer (2006). "Engineered bacteriophage-defence systems in bioprocessing." *Nat Rev Microbiol* 4(5): 395-404.

Tao, L., S. I. Pavlova, et al. (1997). "Analysis of *lactobacillus* products for phages and bacteriocins that inhibit vaginal lactobacilli." *Infect Dis Obstet Gynecol* 5(3): 244-51.

The invention claimed is:

1. A process for the production of bacteriophage for use in control of unwanted bacteria in a fermentation process for conversion of a biomass feed comprising:
   a) taking a first portion of biomass feed from a first biomass feed to the fermentation process;
   b) identifying the most abundant unwanted bacteria in the first portion;
   c) isolating bacteriophage from the first portion taken in step a) that are virulent for at least some of the most abundant unwanted bacteria identified in step b);
   d) culturing at least some of the most abundant unwanted bacteria from the first portion to increase the number of the unwanted bacteria to a first concentration, wherein upon reaction with bacteriophage virulent for said unwanted bacteria and upon subsequent lysis by the bacteriophage, said first concentration produces sufficient bacteriophage that when mixed with the first biomass feed permits the process to achieve a concentration of bacteriophage in the biomass feed of at least $1\times10^4$ pfu; and
   e) producing a solution of bacteriophage isolated in c) and replicated by lysis of the first concentration of bacteria cultured in d);
   wherein the first portion of first biomass feed in step a) is continuously taken from a biomass process feed and an equivalent amount of solution of bacteriophage from step e) is continuously added back to the biomass process feed.

2. The process of claim 1, wherein one or more of the unwanted bacteria are selected from the group consisting of *Lactobacillus, Pediococcus, Lactococcus, Enterococcus, Weissella, Leuconostoc, Streptococcus, Oenococcus, Acetobacter* and *Gluconobacter*.

3. The process of claim 1, wherein one or more of the unwanted bacteria are bacteria other than lactic acid bacteria or acetic acid bacteria.

4. The process of claim 1, wherein the first portion of biomass feed is taken as a sidestream of biomass feed to a biomass process, placed in a reaction vessel in which unwanted bacteria is cultured and mixed with bacteriophage virulent for lactic acid bacteria.

5. The process of claim 1, wherein a nutrient source for bacterial growth is provided to the portion of the biomass feed when culturing said unwanted bacteria.

6. The process of claim 1 wherein unwanted bacteria are added to the portion of the biomass feed when or before adding said bacteriophage to said first biomass portion.

7. The process of claim 1, wherein the biomass feed comprises one or more of sugar, starch, cellulosic feedstock, lignocellulosic feedstock, grains, corn, wheat, milo, barley, millet, sugar cane, sugar beets, molasses, whey, potatoes, agricultural residue, crop residue, bagasse, wheat straw, corn stalks, leaves, husks, forestry residue, logging and mill residue, wood chips, sawdust, pulping liquor, grasses, switchgrass, sorghum, municipal waste, plant waste, animal waste, plant-derived waste, household garbage, paper products, paper pulp, food-processing waste, trees, poplar trees and willow trees.

8. The process of claim 1, further comprising adding a chemical to the unwanted bacterial culture of step d) to prevent growth of the fermentative microorganism.

9. A process for the production of bacteriophage for use in control of *Pseudomonas* or *Vibrio* unwanted bacteria in a fermentation process for conversion of a biomass feed comprising:
   a) taking a first portion of a first biomass feed from biomass feed to the fermentation process;
   b) identifying the most abundant unwanted bacteria of the species in the first portion;
   c) isolating bacteriophage from the first portion taken in step a) that are virulent for at least some of the most abundant *Pseudomonas* or *Vibrio* unwanted bacteria identified in b);

d) culturing at least some of the most abundant *Pseudomonas* or *Vibrio* species unwanted bacteria from the first portion to increase the number of the unwanted bacteria to a first concentration, wherein upon reaction with bacteriophage virulent for said unwanted bacteria and upon subsequent lysis by the bacteriophage, said first concentration produces sufficient bacteriophage that when mixed with the first biomass feed permits the process to achieve a concentration of bacteriophage in the biomass feed of at least $1 \times 10^4$ pfu; and e) producing a solution of bacteriophage isolated in c) replicated by lyse of the bacteria cultured in d);

wherein the first portion of first biomass feed in step a) is continuously taken from a biomass process feed and an equivalent amount of solution of bacteriophage from step e) is continuously added back to the biomass process feed.

10. The process of claim 9 wherein bacteriophage virulent for *Pseudomonas* or *Vibrio* species from sources other than the biomass feed is added to the cultured unwanted bacteria.

11. The process of claim 9, further comprising adding a chemical to the unwanted bacterial culture of step d) to prevent growth of the fermentative microorganism.

* * * * *